US00PP29500P3

(12) United States Plant Patent
Kordes

(10) Patent No.: US PP29,500 P3
(45) Date of Patent: Jul. 17, 2018

(54) FLORIBUNDA ROSE PLANT NAMED 'KORGERIORA'

(50) Latin Name: *Rosa hybrida*
Varietal Denomination: KORgeriora

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 1 day.

(21) Appl. No.: 15/330,270

(22) Filed: Sep. 1, 2016

(65) Prior Publication Data

US 2018/0064007 P1 Mar. 1, 2018

(51) Int. Cl.
*A01H 5/02* (2018.01)

(52) U.S. Cl.
USPC ..... Plt./146

CPC ..... *A01H 5/0222* (2013.01)

(58) Field of Classification Search
USPC ..... Plt./101, 102, 105, 116, 119, 123, 126, Plt./130, 135, 141, 146
See application file for complete search history.

(56) References Cited

PUBLICATIONS

The World Federation of Rose Societies. Rost Trials in Baden B. Wien, Austria. http://www.worldrose.org/trials/2016/austria/austria9.asp. 1 page.*

* cited by examiner

*Primary Examiner* — Susan McCormick Ewoldt
*Assistant Examiner* — Karen M Redden
(74) *Attorney, Agent, or Firm* — Samuel R. McCoy, Jr.

(57) ABSTRACT

'KORgeriora' is a new and distinct variety of *Rosa hybrida* which is characterized by the combination of an upright to bushy growth habit, moderate plant vigor, excellent resistance to powdery mildew and black spot disease, and panicles of one to eight very-double orange flowers with a light floral fragrance. The new variety propagates successfully by stem cuttings and grafting and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORgeriora'.

BACKGROUND OF THE INVENTION

Parentage: The *Rosa hybrida* variety 'KORgeriora' is the result of a controlled cross-pollination breeding program carried out by the inventor in Klein Offenseth-Sparrieshoop, Germany. The objective of the said breeding program was to create a new and distinct rose plant with unique qualities, such as:

1. Uniform growth and flowering; and
2. Abundant, recurrent orange flowers; and
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORgeriora' from all other varieties known to the inventor.

'KORgeriora' is a seedling selection which resulted from the controlled pollination of *Rosa hybrida* 'KORaruli' (U.S. Plant Pat. No. 22,352), the seed parent, and *Rosa hybrida*

'KORfocgri' (U.S. Plant Pat. No. 22,353), the pollen parent, during the summer of 2006. As part of a rose development program, Tim-Hermann Kordes germinated seeds from the aforementioned hybridization during the following winter and conducted evaluations and observations on the resulting seedlings in a controlled environment in Klein Offenseth-Sparrieshoop, Germany. The resulting seedlings exhibited distinctive physical and biological characteristics. The new rose plant was selected as a single plant in May of 2007 from the seedling beds due to its superior characteristics and asexually propagated for further evaluation. This new and distinctive rose variety was given the name 'KORgeriora'.

Asexual Reproduction: 'KORgeriora' was first asexually propagated by bud grafting in July of 2007 at the inventor's nursery in Klein Offenseth-Sparrieshoop, Germany. Subsequently, 'KORgeriora' has been successfully propagated by stem cuttings and bud grafting in Jackson County, Oreg. These initial and other subsequent propagations conducted in controlled environments demonstrate that 'KORgeriora' reproduces true to type in successive generations of asexual reproduction.

SUMMARY OF THE INVENTION

The following characteristics have been repeatedly observed and represent the distinguishing characteristics of the new *Rosa hybrida* cultivar 'KORgeriora'. These traits, in combination, distinguish 'KORgeriora' as a new and distinct cultivar.

1. *Rosa hybrida* 'KORgeriora' exhibits a moderately vigorous growth rate; and
2. *Rosa hybrida* 'KORgeriora' exhibits an upright to bushy growth habit; and
3. *Rosa hybrida* 'KORgeriora' exhibits panicles bearing one to eight orange flowers; and
4. *Rosa hybrida* 'KORgeriora' exhibits large, very-double flowers with a light floral fragrance; and
5. *Rosa hybrida* 'KORgeriora' exhibits excellent resistance to powdery mildew and black spot diseases.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORgeriora', taken from a one year old plant.

DETAILED BOTANICAL DESCRIPTION

The following is a detailed botanical description of a new and distinct variety of *Rosa hybrida* known as 'KORgeriora', based upon observations made in August of 2016 of one year old, field-grown plants in Jackson County, Oreg. Those skilled in the art will appreciate that certain characteristics will vary with older or, conversely, with younger plants. 'KORgeriora' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORgeriora' and comparisons with the parents and closest known comparator variety of *Rosa hybrida* are provided below.

General plant description:

*Growth rate.*—Moderately vigorous.

*Growth habit.*—Upright to bushy.

*Mature dimensions.*—70 cm tall and 50 cm wide, on average.

*Cold hardiness.*—Grown successfully in USDA Hardiness Zones 5.

*Propagation.*—Stem cuttings and bud grafting.

*Disease resistance.*—Excellent resistance to powdery mildew (*Sphaerotheca pannosa*) and blackspot (*Diplocarpon rosae*) diseases under normal growing conditions in Jackson County, Oreg.

Root system:

*Type.*—Fibrous root system.

*Branching.*—Moderately branched.

*Density.*—Moderately dense.

*Color.*—Greyed-yellow Group 161D.

*Distribution.*—Roots distributed evenly throughout the soil profile, from shallow to deep.

Stems:

*Stem color.*—Young stems are Yellow-Green Group 146B; mature stems are Yellow-Green Group 146B.

*Anthocyanin intonations.*—Intonations of Greyed-Purple Group 183D are present on young stems.

*Stem surface texture.*—Both young stems and mature stems are smooth.

*Stem dimensions.*—Typical mature stems are approximately 400 mm long and 8.0 mm in diameter.

*Prickles.*—Incidence — Typically 7 prickles per 10 cm of stem. Size — Average length is 5.0 mm long. Immature prickle color — Greyed-Orange Group 165A. Mature prickle color — Greyed-Orange Group 166C. Anthocyanin intonations — Intonations of Greyed-Orange Group 176B present on immature prickles. Shape — Concave. Texture — Smooth.

Leaves:

*Arrangement.*—Imparipinnate compound leaves; mature axillary leaves consisting of 7 leaflets.

*Attachment.*—Petiolate.

*Dimensions.*—140 mm long and 100 mm wide.

*Abundance.*—Average; approximately 70 leaves.

*Stipules.*—Size — 10 mm long and 4.0 mm wide. Stipule color — Yellow-Green Group 146C. Anthocyanin intonations — Intonations of Greyed-Red Group 184C are present on both surfaces of the juvenile stipules. Stipitate glands — A limited number of stipitate glands are present on the abaxial surface; abundant along the margins. Margins — Serrulate, with stipitate glands. Texture, adaxial surfaces — Glabrous. Texture, abaxial surfaces — Rugose. Apex — Apiculate. Base — Flat.

*Petiole.*—Length — Average 6.0 mm. Diameter — Average 2.0 mm. Petiole color, adaxial surface — Yellow-Green Group 146C. Petiole color, abaxial surface — Yellow-Green Group 146B. Anthocyanin intonations — Intonations of Greyed-Red Group 181C are present on both surfaces of the juvenile foliage. Margins — Without stipitate glands. Prickles — One prickle is present. Stipitate glands — Very occasional on the abaxial surface only. Texture — Glabrous. Strength — Moderately strong.

*Rachis.*—Length — Average of 15 mm. Diameter — Average 1.5 mm. Color — Yellow-Green Group 146A. Anthocyanin intonations — Greyed-Purple Group 185B. Margins — With the occasional stipitate gland. Prickles — A few small prickles underneath. Stipitate glands — A limited number of stipitate glands are present. Texture — Glabrous.

*Leaflets.*—Dimensions — Average size of the terminal leaflet is 50 mm long and 30 mm wide. Shape — Ovate. Apex — Acute. Base — Obtuse. Margins — Finely serrated; slightly undulated. Luster, texture and pubescence; adaxial surface — Semi-glossy, smooth and glabrous. Luster, texture and pubescence; abaxial surface — Matte, leathery and glabrous. Juvenile foliage color, adaxial surface — Yellow-Green Group 146A. Juvenile foliage color, abaxial surface — Yellow-Green Group 146D. Mature foliage color, adaxial surface — Green Group 137A. Mature foliage color, abaxial surface — Yellow-Green Group 146B. Anthocyanin intonations — In juvenile foliage, intonations of Greyed-Purple Group 177A to 177C are present throughout the adaxial and abaxial surfaces. Venation — Reticulate. Petiolule — Dimensions — 3.0 mm long and 1.0 mm in diameter. Petiolule color, adaxial surface — Green Group 137A. Petiolule color, abaxial surface — Yellow-Green Group 146C. Prickles — A few small prickles are present. Texture, adaxial surface — Leathery; pubescent. Texture, abaxial surface — Smooth. Margins — With a moderate number of stipitate glands present on the upper margin.

Inflorescence:

*Inflorescence type.*—Panicles with 1 to 8 flower buds. Flowers are held upright.

*Blooming habit.*—Recurrent; floriferous.

*Size.*—90 mm tall and 130 mm wide, on average.

*Peduncle.*—Length — 50 to 70 mm average length. Diameter — 3.0 to 4.0 mm average diameter. Color — Yellow-Green Group 146C. Anthocyanin intonations — None present. Strength — Strong. Texture and pubescence — Glabrous.

Flowering laterals: Present below the initiation of inflorescence. Generally 1 to 2 flowering laterals are present, with 1 to 3 flowers per flowering shoot.

Bud:

*Bud form.*—Short; globular.

*Size.*—Upon opening, 25 mm in length from base of receptacle to distal end of bud and 20 mm diameter at its widest point.

*Texture.*—Smooth.

*Color, as sepals first unfold.*—Orange-Red Group N30C.

*Color when one-quarter open, inner side.*—Orange-Red Group N30A.

*Color when one-quarter open, outer side.*—Orange-Red Group N30A.

Flower:

*Pedicel.*—Length — 25 to 50 mm average length. Diameter — 2.0 to 3.0 mm average diameter. Color — Yellow-Green Group 146B. Anthocyanin intonations — Greyed-Purple Group 183C to 183D. Strength — Moderately strong. Texture and pubescence — Smooth and glabrous.

*Calyx.*—General — Comprised of five polysepalous sepals, with strong foliaceous appendages present on three of the five sepals. Diameter of calyx — 60 to 65 mm, at anthesis. Sepals — Color, upper surface — Green Group 138B. Color, lower surface — Green Group 138A. Anthocyanin intonations — Intonations of Greyed-Purple Group 183C are present on the lower surface. Size — Varied; 25 to 40 mm and 8 to 10 mm wide, on average. Apex — Cirrose to apiculate. Base — Flat at union with receptacle. Quantity — Five. Upper surface — Pubescent. Lower surface — Smooth to slightly coriaceous. Margins — With a moderate number of stipitate glands. Some sepals are slightly pubescent at the margins. Stipitate glands — A limited number of stipitate glands are present on the lower surface of a few sepals.

*Corolla.*—Habit; type — Very-double. General shape of corolla — Open cup; shallow. Shape of corolla when viewed from the side — Upon opening, upper portion — Convex. Upon opening, lower portion — Flat. Open flower, upper portion — Flattened convex. Open flower, lower portion — Flat. Dimensions — Large size for a floribunda rose. When open, the average flower diameter is 75 to 80 mm and the average flower height is 35 mm. Fragrance — Light floral fragrance. Duration — On the plant for 5 to 6 days. Senesced petals drop away cleanly. Petals — Petal count — Exhibits very double flowers with more than 125 petals under normal conditions. Petal reflex — Petals are somewhat reflexed. Timing of petal reflex — Simultaneous. Petal margin — Entire. Petal shape — Obovate. Apex — Obtuse. Base — Cuneate. Dimensions — 18 to 25 mm long and 12 to 25 mm wide. Texture, inner surface — Smooth. Texture, outer surface — Smooth. Petal color, upon opening — Outermost petals, inner surface — Orange-Red Group N30A. Outermost petals, outer surface — Red Group 37A. Innermost petals, inner surface — Orange-Red Group N30A. Innermost petals, outer surface — Orange-Red Group N30B. Basal petal spots, upon opening — Outermost petals — Color, inner surface — Green-Yellow Group 1B. Color, outer surface — Green-Yellow Group 1A. Dimensions — 4.0 mm wide and 5.0 mm tall. Innermost petals — Color, inner surface — Green-Yellow Group 2B. Color, outer surface — Green-Yellow Group 2B. Dimensions — 4.0 mm wide and 5.0 mm tall. Petal color, after opening — Outermost petals, inner surface — Red Group 41B. Outermost petals, outer surface — Red Group 41D. Innermost petals, inner surface — Red Group 40D. Innermost petals, outer surface — Orange-Red Group 33C. Basal petal spots, after opening — Outermost petals — Color, inner surface — Yellow Group 3C. Color, outer surface — Yellow Group 2C. Dimensions — 6.0 mm wide and 5.0 mm tall. Innermost petals — Color, inner surface — Yellow Group 2B. Color, outer surface — Yellow Group 2C. Dimensions — 4.0 mm wide and 5.0 mm tall. General Tonality — On open flower, Red Group 40B. No change in general tonality at the end of the fourth day; thereafter the general tonality is Red Group 41C. Petaloids — Quantity — Approximately 40 petaloids per flower, on average. Dimensions — Approximately 5.0 to 17 mm long and 3.0 to 5.0 mm wide. Color, inner surface — Orange-Red Group 32A. Color, outer surface — Orange-Red Group 32A. Margins — Very irregular; entire to undulated to indented to folded. Shape — Irregular; obovate to lanceolate to oblanceolate. Apex — Acute to obtuse. Base — Cuneate to attenuate. Texture, inner and outer surfaces — Smooth.

Reproductive organs:

*Stamens.*—Quantity — Approximately 50, on average, and regularly arranged around the styles. Anthers — Shape — Reniform. Dimensions — 2.0 mm long and 1.0 mm wide, on average. Color — Greyed-Orange Group N167A. Pollen — Present; moderately abundant. Color is Greyed-Orange Group 175B. Filaments — Color — Yellow Group 12A. Length — 5.0 mm.

*Pistils.*—Quantity — Average; approximately 24. Stigmas — Size — 2.0 mm. Location — Inferior in position to anthers. Color — Yellow Group 1B. Styles — Length — Approximately 4.0 mm long. Color — Yellow-White Group 158C, with intonations of Greyed-Red Group 179D.

*Ovary.*—Dimensions — 7.0 mm long and 4.0 mm in diameter. Color — White Group 155A.

*Receptacle.*—Shape — Urn-shaped. Dimensions — Approximately 8.0 mm high and 7.0 mm wide. Surface texture and pubescence — Smooth and glabrous. Color — Yellow-Green Group 146B. Anthocyanin intonations — Greyed-Purple Group 183B.

Hips and seed formation: Not observed to date.

COMPARISONS WITH THE PARENTS

The new rose plant may be distinguished from its seed parent, *Rosa hybrida* 'KORaruli', by the characteristics described in Chart 1.

CHART 1

| Characteristic | 'KORgeriora' | 'KORaruli' |
|---|---|---|
| Growth habit. | Upright to bushy. | Upright. |
| Flower color. | Orange. | Yellow. |
| Bud form. | Short; globular. | Long; high-centered. |

The new rose plant may be distinguished from its pollen parent, *Rosa hybrida* 'KORfocgri', by the characteristics described in Chart 2.

CHART 2

| Characteristic | 'KORgeriora' | 'KORfocgri' |
|---|---|---|
| Foliage. | Dark green; glossy. | Green; very glossy. |
| Flower color. | Orange. | Salmon-orange, suffused with yellow. |
| Flower type; petal count. | Very double. | Double. |

COMPARISON WITH THE MOST SIMILAR *ROSA* CULTIVAR KNOWN TO THE INVENTOR

For a comparison, several physical characteristics of the *Rosa hybrida* cultivar 'KORfloci109', a rose cultivar from the same inventor, U.S. patent application Ser. No. 15/330,187, are compared to 'KORgeriora' in Chart 3.

CHART 3

| Characteristic | 'KORgeriora' | 'KORfloci109' |
|---|---|---|
| Growth habit. | Upright to bushy. | Compact. |
| General tonality of the open flower. | Red Group 40B. | Orange-Red Group 32B. |
| Flower type; petal count. | More than 125. | 75. |

That which is claimed:

1. A new and distinct variety of rose plant named 'KORgeriora', as described and illustrated herein.

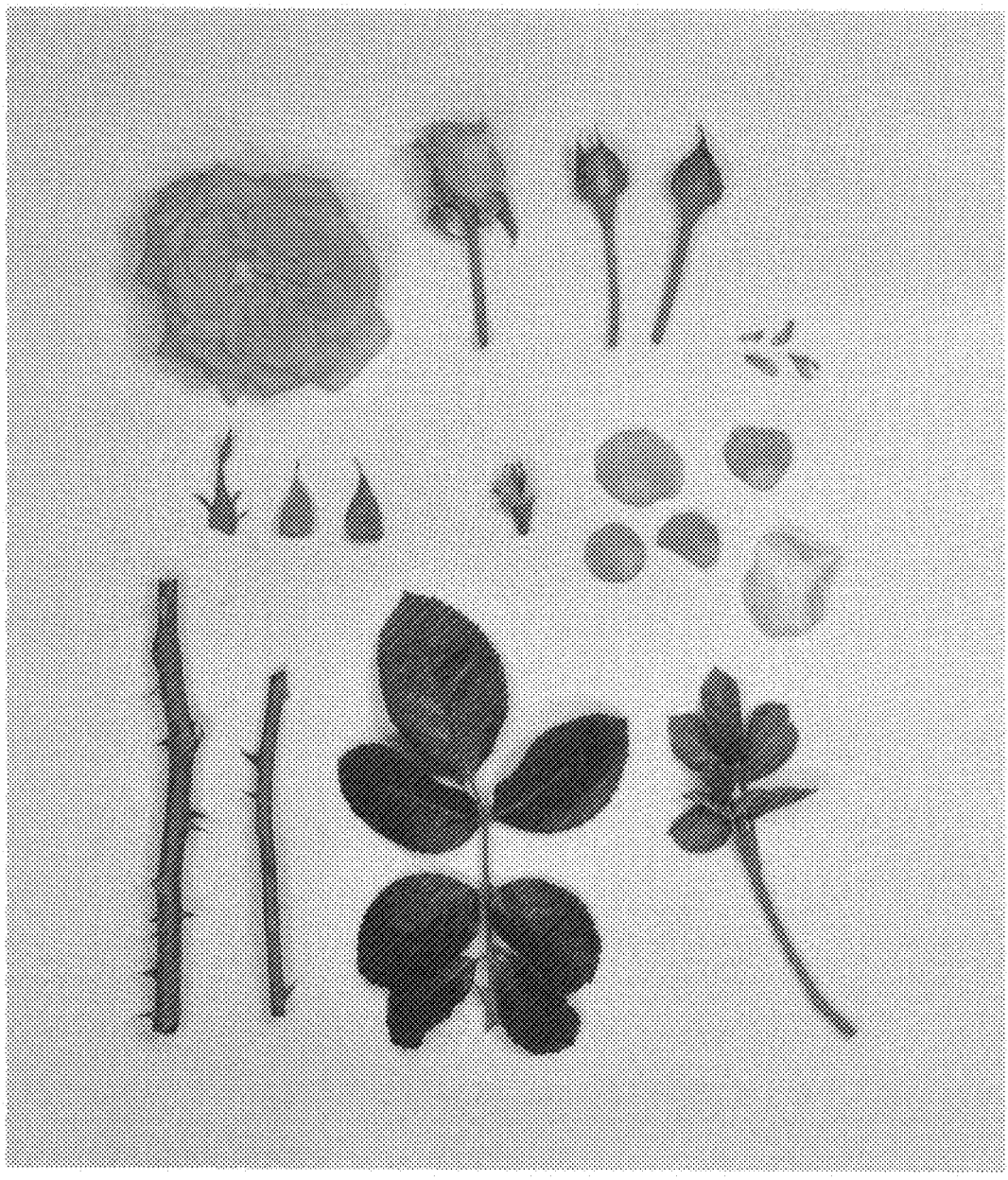

* * * * *